(12) United States Patent
Badmaev

(10) Patent No.: US 10,864,174 B2
(45) Date of Patent: Dec. 15, 2020

(54) METHOD MAINTAINING IRON HOMEOSTASIS WITH SHOGAOLS

(71) Applicant: Vladimir Badmaev, Staten Island, NY (US)

(72) Inventor: Vladimir Badmaev, Staten Island, NY (US)

( * ) Notice: Subject to any disclaimer, the term of this patent is extended or adjusted under 35 U.S.C. 154(b) by 42 days.

(21) Appl. No.: 16/096,595

(22) PCT Filed: Apr. 26, 2017

(86) PCT No.: PCT/US2017/029622
§ 371 (c)(1),
(2) Date: Oct. 25, 2018

(87) PCT Pub. No.: WO2017/189717
PCT Pub. Date: Nov. 2, 2017

(65) Prior Publication Data
US 2019/0133967 A1 May 9, 2019

Related U.S. Application Data

(60) Provisional application No. 62/328,499, filed on Apr. 27, 2016.

(51) Int. Cl.
*A61K 31/12* (2006.01)
*A61K 36/906* (2006.01)
*A61K 36/28* (2006.01)
*A61K 36/185* (2006.01)
*A61K 36/47* (2006.01)

(52) U.S. Cl.
CPC ............ *A61K 31/12* (2013.01); *A61K 36/185* (2013.01); *A61K 36/28* (2013.01); *A61K 36/47* (2013.01); *A61K 36/906* (2013.01)

(58) Field of Classification Search
None
See application file for complete search history.

(56) References Cited

U.S. PATENT DOCUMENTS

| | | | |
|---|---|---|---|
| 5,760,010 | A | 6/1998 | Klein |
| 2008/0207569 | A1 | 8/2008 | Spada |
| 2011/0039886 | A1 | 2/2011 | Klaus et al. |
| 2011/0229590 | A1 | 9/2011 | Kim et al. |
| 2016/0017032 | A1 | 1/2016 | Westerman et al. |

FOREIGN PATENT DOCUMENTS

| | | |
|---|---|---|
| WO | 2005082459 | 9/2005 |
| WO | 2014071015 A1 | 5/2014 |

OTHER PUBLICATIONS

Kumar et al., Anti-Inflammatory Action of Ginger: A Critical Review in Anemia of Inflammation and its Future Aspects. International Journal of Herbal Medicine, vol. 1, Issue 4, 2013 (retrieved on Oct. 25, 2018).

*Primary Examiner* — Susan Hoffman
(74) *Attorney, Agent, or Firm* — Werschulz Patent Law, LLC; Patricia P. Werschulz, Esq.

(57) ABSTRACT

Composition of shogaols and related compounds from Zingiberaceae family of plants for improved iron metabolism in health and prevention iron overload in patients in need of nutritional and/or therapeutic approach to ameliorate iron-overload.

20 Claims, No Drawings

METHOD MAINTAINING IRON HOMEOSTASIS WITH SHOGAOLS

This is a National Phase Application filed under 35 U.S.C. § 371 as a national stage of PCT/US2017/029622, filed on Apr. 26, 2017, an application claiming the benefit under 35 U.S.C. § 119(e) of U.S. Provisional Application No. 62/328,499, filed on Apr. 27, 2016 and claims priority thereof, the content of each of which is hereby incorporated by reference in its entirety.

FIELD OF INVENTION

The present invention relates to method use polyphenolic compounds extracted from *Zingiber* sp., especially shogaols in nutritional and/or pharmacologic prevention and treatment of detrimental health consequences of high levels of circulating and tissue iron. The invention is also directed to method of optimal utilization of iron for human health and iron homeostasis.

BACKGROUND OF INVENTION

Diseases and health conditions associated with iron deficiency and iron overload are prevalent across the world. Maintaining proper levels of body iron is critical for hemoglobin synthesis. Diseases like myelodysplastic syndromes (MDS) requiring regular blood transfusions typically lead to iron overload and without proper treatment lead to significant morbidity and mortality.

MDS is a heterogeneous group of disorders characterized by ineffective hematopoiesis. In current invention, MDS exemplifies a condition with risk of iron overload due to need for frequent blood cell transfusions. Chelating excess iron from the overload prevents reactive oxygen species (ROS) and may induce healthy hematopoietic cell differentiation which is compromised in MDS. In clinical practice, it has been recognized that chelation therapy in MDS patients ameliorates pathological effects of excess iron and oxidative stress by decreasing iron-induced cytotoxicity, DNA damage, blocked differentiation in hematopoietic cells, and possibly transformation to leukemia.

Effective management of iron overload results in excretion of unbound circulating iron and or activates system(s) or mechanisms of removal excess iron from the body. The examples of currently available chelating agents include deferoxamine, deferasirox and deferiprone which bind with iron in the bloodstream and enhance its elimination in urine and feces. However, current generation of chelating agents can result in nephrotoxicity and liver toxicity.

One of the important mechanisms of iron homeostasis depends on the liver manufactured hormone hepcidin which regulates proteins transporting iron in the body, i.e. transferrin—a protein that carries iron to target tissues, ferritin—a cellular iron storage protein, and ferroportin which exports iron from the body. Hepcidin synthesis and secretion by the liver is controlled by iron stores, lingering inflammatory process, hypoxia, erythropoiesis and nutritional factors, e.g. vitamin D.

In states in which the hepcidin level is abnormally high such as inflammation, serum iron falls due to iron trapping within macrophages and liver cells and decreased gut iron absorption. Hepcidin degrades iron transporting proteins and prevents iron gastrointestinal absorption and systemic utilization. When the hepcidin level is abnormally low such as in hemochromatosis, iron overload occurs due to decreased iron efflux.

When transferrin's and ferritin iron-binding capacity is exceeded, non-transferrin-bound iron (NTBI) is produced. The unbound circulating iron ion causes cellular damage via production of reactive oxygen species (ROS) which oxidize lipids, proteins, and nucleic acids, resulting in premature apoptosis, cell death, tissue and organ damage (e.g., iron-overload-associated liver cirrhosis, diabetes and other endocrinopathies, and cardiomyopathy)—contributing to increased morbidity and mortality in patients requiring regular blood transfusions.

The current invention is based on the study designed to test the efficacy of shogaols, compounds derived from ginger roots (*Zingiber officinale* Roscoe, Zingiberaceae) chemically related to gingerols, in improving the cytopenias of patients with low and intermediate-1 risk myelodysplastic syndromes or MDS.

Shogaols, the dehydration products of corresponding gingerols during storage or thermal processing, are different from gingerols chemically and in their biological properties. In the in vitro study, shogaols had much stronger growth inhibitory effects than gingerols on H1299 human lung cancer cells and HCT-116 human colon cancer cells, especially prominent when comparing [6]-shogaol with [6]-gingerol ($IC_{50}$: ~8 µM vs. ~150 µM). In addition, it was found that [6]-shogaol had much stronger inhibitory effects on the arachidonic acid pathway and nitric oxide (NO) synthesis than [6]-gingerol.

EXPERIMENTAL DESIGN

The low and Intermediate-1 risk MDS patients were selected to receive shogaols standardized for 25% shogaols extracted from ginger roots with the CO2 supercritical extraction method. The rationale for using shogaols has been that it is a natural, non-toxic substance with anti-tumor, anti-proliferative and chemopreventive properties which are likely to be well tolerated in MDS elderly, population. The shogaols were intended as chemopreventive and therapeutic modality and to look for improvement in cytopenias in the treated patients.

Treatment protocol: Six patients, 2 women and 4 men, mean age 70 years old with a confirmed diagnosis of low or Intermediate-1 risk myelodysplastic syndromes were eligible for this trial. No other experimental agent aimed at treating MDS was allowed during the period of protocol therapy. Therapy has been continued unless there were signs of disease progression. Supportive care measures including the use of transfusions have been permitted during the protocol duration. The dose of 20 mg/day ginger root extract standardized for approximately 25% shogaols in form of soft-gel capsule was administered once a day for up to 12 months.

The study protocol comprises the following steps:

A) Identifying Low/Intermediate-1 Risk MDS patients and entering said patients into the study;

B) Starting Shogaols at a dose of 20 mg/day ginger extract standardized for 25% shogaols;

C.) Evaluating for response in bi-monthly intervals for 6 and 12 months; and

D.) Continuing therapy for one year or unless disease is progressing. Responders may continue for as long as they continue to experience benefit.

The six selected for the study patients were monitored at 2 month intervals for a period of 6 and 12 months. The study product was disposed in white opaque bottles each 60 capsules. Each bottle with a label indicating: Shogaols 25%

(Extract of Zingiber officinale roots) in soft-gel capsules—20 mg per capsule. Use 1 capsule a day with a meal.

TABLE I. Hematologic results in 6 MDS patients (mean values) receiving daily 20 mg shogaols 25% per day for 6 months.

TABLE II. Individual ferritin levels (normal=30-300 ug/L) in six patients over 6 month shogaols administration.

TABLE III. Individual ferritin levels (normal=30-300 ug/L) in patients over 6 and 12-month shogaols administration.

TABLE IV. Hematologic and liver function tests data in patient No. 1 during 6 and 12-month shogaols administration.

RESULTS

Administration of ginger root (*Zingiber officinale* Roscoe) extract standardized for 25% shogaols for 6 and 12 months 20 mg/day to MDS patients showed no grounds to discontinue the supplement, with no objective or subjective side effects, and in three out of six patients a significant reduction in ferritin levels comparing to the baseline levels. In addition, there was a significant reduction in mean values from 6 patients in the reticulocyte count and the liver enzyme levels in a selected patient with a highest drop in ferritin levels. These results with the shogaols therapy have not been previously reported and provide grounds for the novel use of shogaols as a nutritional and therapeutic support for patients in need of preventing iron overload and improving iron homeostasis.

DESCRIPTION OF THE INVENTION

The natural components extracted from ginger (*Zingiber officinale*) roots, especially shogaols, show an unexpected and previously unknown properties in regulating iron homeostasis in hematologic patients and potentially healthy subjects in need of safe and optimal iron utilization in the body. Shogaols were evaluated for their potential clinical usefulness in patients with myelodysplastic syndromes (MDS), which may exemplify iron overload condition and its impact on the overall health. The iron overload is a common outcome and side effect of frequent blood transfusions, which are required in hematologic patients to prevent anemia and enhance hematopoiesis. The excess iron from red blood cells, may result in build-up of free circulating iron ion which generates reactive oxygen species (ROS) related pathology. The ROS pathology leads to increased morbidity in MDS patients, e.g. compromised liver and other organs functions. Without being bound to any particular theory, it is hypothesized that shogaols which are potent anti-inflammatory compounds may act as hypomethylating agents of major proteins required to transport iron and may this way ameliorate iron overload. The other plausible hypothesis is that shogaols may upregulate or downregulate levels of hepcidin, a liver hormone, which is responsible for decreasing levels of proteins responsible for iron transport and storage in the body. Shogaols may also prevent iron-caused mutation of genes responsible for expression of Human Hemochromatosis protein (HFE) which controls transferrin, a major carrier of iron in the body, and prevents mutation of genes responsible for progression of the hematologic pathology, potentially acting as the chemopreventive and therapeutic agent. The invention provides shogaols which in course of 12 months of daily administration to the MDS patients did not affect adversely patients' condition and health, while significantly lowering the following condition-elevated hematologic parameters: ferritin levels, reticulocyte count and liver function tests. In addition, it is proposed that shogaols may contribute to the optimal utilization of iron in healthy individuals.

FORMULATIONS

When used in a preparation for oral administration, and without being bound to a specific recipe, the shogaols of invention maybe used at a daily dose of approximately 0.1-0.6 mg/kg of body weight, or, alternatively, at a dose of about 5 mg to 50 mg per day for an average adult. For best therapeutic results the shogaols may be combined with components from *Terminalis chebula* fam, Combretaceae, *Terminalia bellerica* fam. Combretaceae, *Emblica officinalis* fam. Euphrobiaceae, *Inula helenium* fam. Compositae, *Rheum palmatum* fam Polygonaceae, *Gentiana lutea* fam. Gentianaceae, sodium sulfate, sodium chloride and sodium bicarbonate.

The compositions of the present invention may also include suitable excipients, fillers and formulations e.g. microencapsulation, nanotechnology which facilitate gastrointestinal absorption and target tissue and receptor site bioavailability. The formulation may also include suitable technology for a parenteral delivery system.

The herbal compounds of invention are generally in form of a "Green technology" solvent-free extraction prepared with the supercritical CO2 extraction or adiabatic extraction with methane or butane. The herbal compounds of invention, e.g. shogaols can be obtained through a chemical synthesis.

TABLE I

| variable | Baseline(n = 6) | Month 2(n = 6) | Month 4(n = 6) | Month 6(n = 5) |
| --- | --- | --- | --- | --- |
| Hb (128-175 g/L) | 115.2 ± 28.7 | 118 ± 24 | 117.3 ± 23.5 | 114 ± 28.2 |
| RCC (4.2-6.2 × $10^{12}$/L) | 3.6 ± 1.1 | 3.7 ± 1 | 3.7 ± 1 | 3.5 ± 1.1 |
| Hct (0.36-0.53) | 0.35 ± 0.09 | 0.36 ± 0.07 | 0.36 ± 0.08 | 0.35 ± 0.09 |
| MCV (80-100 fL) | 98.5 ± 9.5 | 98.3 ± 8.8 | 99.2 ± 9.5 | 100 ± 9.2 |
| MCH (27-32 pg) | 32.7 ± 3.3 | 32.6 ± 3.6 | 32.6 ± 3.6 | 32.9 ± 3.6 |
| MCHC (310-360 g/L) | 330.8 ± 13.8 | 331.5 ± 9.2 | 328.8 ± 10 | 328.2 ± 8.9 |
| RDW (10-15) | 17.6 ± 5.2 | 17.9 ± 5.4 | 17.8 ± 5.3 | 18.7 ± 5.5 |
| WCC (4-11 × 109/L) | 5.1 ± 1.6 | 5 ± 2 | 4.4 ± 1.6 | 5 ± 2.8 |
| Neut (2-7.5 × 109/L) | 2.1 ± 0.8 | 2.1 ± 1 | 1.8 ± 0.9 | 2 ± 0.8 |
| ALC (1-4 × 109/L) | 2 ± 1 | 1.7 ± 0.8 | 1.7 ± 0.8 | 1.7 ± 1 |
| Pltlts (150-450 × 109/L) | 191.7 ± 149.8 | 165.2 ± 163.4 | 154.3 ± 149 | 185.4 ± 168 |
| Retic (20-100) | 71.7 ± 53.4 | 55.6 ± 32.2 | 56.3 ± 39.6 | 52.4 ± 27.3 |
| % retic | 2.1 ± 1.8 | 1.5 ± 0.7 | 1.5 ± 0.9 | 1.5 ± 0.5 |
| Iron (5-30 umol/L) | 23.4 ± 7 | 22 ± 9.3 | 24.8 ± 9.1 | 27.1 ± 10.5 |
| Transferrin(2-3.2 g/L) | 2.2 ± 0.5 | 2.2 ± 0.5 | 2.2 ± 0.5 | 2.3 ± 0.3 |

TABLE I-continued

| variable | Baseline(n = 6) | Month 2(n = 6) | Month 4(n = 6) | Month 6(n = 5) |
| --- | --- | --- | --- | --- |
| TIBC (46-70 umol/L) | 47 ± 7.1 | 47.8 ± 8.4 | 47.8 ± 7.7 | 50 ± 7.2 |
| Ferritin (30-300 ug/L) | 625.7 ± 797.8 | 517.8 ± 739.5 | 440 ± 551.1 | 416.4 ± 378 |
| % saturation (10-45%) | 49.3 ± 19.8 | 48.2 ± 28.8 | 53.2 ± 24.2 | 56.2 ± 22.7 |

TABLE II

| Patient no. | Baseline | Month 2 | Month 4 | Month 6 | % change from baseline |
| --- | --- | --- | --- | --- | --- |
| 1 | 2195 | 2017 | 1537 | 1071 | −51 |
| 2 | 222 | 219 | 196 | 275 | |
| 3 | 709 | 379 | 448 | 387 | −45 |
| 4 | 94 | 148 | 114 | 122 | |
| 5 | 336 | 139 | 117 | | −65 |
| 6 | 198 | 205 | 228 | 227 | |

TABLE III

| Pt no. | bsl | M2 | M4 | M6 | % ch f bsl | ps | ps | Bsl2 | M2 | M4 | M6 | % ch fr bsl |
| --- | --- | --- | --- | --- | --- | --- | --- | --- | --- | --- | --- | --- |
| 1 | 2195 | 2017 | 1537 | 1071 | −51 | | | 1057 | 1057 | 935 | 967 | 929 −58 |
| 2 | 222 | 219 | 196 | 275 | 24 | | | | | | | |
| 3 | 709 | 379 | 448 | 387 | −45 | 413 | 545 | 664 | 428 | 510 | 390 | −45 |
| 4 | 94 | 148 | 114 | 122 | 30 | | | | | | | |
| 5 | 336 | 139 | 117 | | −65 | | | | | | | |
| 6 | 198 | 205 | 228 | 227 | 15 | | | | | | | |

TABLE IV

| | Bsl1 | M2 | M4 | M6 | Bsl2 | M2 | M4 | M6 | % ch fr bsl |
| --- | --- | --- | --- | --- | --- | --- | --- | --- | --- |
| ferritin | 2195 | 2017 | 1537 | 1071 | 1057 | 935 | 967 | 929 | −58 |
| GGT(5-50 U/L) | 151 | 132 | 132 | 137 | 117 | 116 | 110 | 123 | −19 |
| ALT(5-40 U/L) | 80 | 81 | 59 | 43 | 54 | 49 | 39 | 38 | −53 |
| AST(10-40 U/L) | 70 | 73 | 51 | 48 | 48 | 47 | 37 | 42 | −40 |
| Iron (5-30 umol/L) | 28 | 17.6 | 35.7 | 35.9 | 39.8 | 25.5 | 43.4 | 27.9 | 0 |
| TIBC(46-70 umol/L) | 56 | 58 | 54 | 58 | 60 | 56 | 54 | 56 | 0 |
| % srn(10-45%) | 50 | 30 | 66 | 62 | 66 | 46 | 80 | 50 | 0 |

We claim:

1. A method of treating an overload of hematologic iron, comprising administering daily an effective amount of shogaols to an individual.

2. The method as described in claim 1, further comprising daily administering an amount of ginger root extract having the effective amount of shogaols.

3. The method as described in claim 2, wherein the amount of ginger root extract is standardized for a minimum of twenty-five (25) percent shogaols.

4. The method as described in claim 1, wherein the daily amount of shogaols is approximately 0.1-0.6 mg shogaols per kg body weight administered orally.

5. The method as described in claim 1, wherein the daily amount of shogaols is administered parenterally.

6. The method as described in claim 1, wherein the amount of shogaols administered daily is 20 mg.

7. The method as described in claim 6, further comprising administering the effective amount of shogaols daily to an individual in treatment for a myelodysplastic condition.

8. The method as described in claim 6, wherein administering the effective amount of shogaols daily to the individual decreases serum ferritin.

9. The method as described in claim 6, wherein administering the effective amount of shogaols daily to the individual decreases reticulocyte count.

10. The method as described in claim 6, wherein administering the effective amount of shogaols daily to the individual decreases liver enzyme levels.

11. The method as described in claim 6, wherein administering the effective amount of shogaols daily to the individual regulates serum hepcidin levels.

12. The method as described in claim 6, wherein administering the effective amount of shogaols daily to the individual hypomethylates major proteins required for transportation of iron.

13. A method of preventing an overload of hematologic iron, comprising administering daily an effective amount of shogaols to an individual who is at risk of developing an overload of hematologic iron.

14. The method as described in claim 13, further comprising administering the effective amount of shogaols daily to an individual in treatment for a myelodysplastic syndrome who is at risk of developing an overload of hematologic iron.

15. The method as described in claim 13, wherein administering the effective amount of shogaols daily to the individual who is at risk of developing an overload of hematologic iron decreases serum ferritin for said individual.

16. The method as described in claim 13, wherein administering the effective amount of shogaols daily to the individual who is at risk of developing an overload of hematologic iron decreases reticulocyte count for said individual.

17. The method as described in claim 13, wherein administering the effective amount of shogaols daily to the individual who is at risk of developing an overload of hematologic iron decreases liver enzyme levels for said individual.

18. The method as described in claim 13, wherein administering the effective amount of shogaols daily to the individual who is at risk of developing an overload of hematologic iron regulates serum hepcidin levels for said individual.

19. A method of treating an overload of hematologic iron, comprising orally administering an effective amount of shogaols to an adult individual at a dose of about 5 mg to 50 mg per day.

20. The method of claim 19, wherein the effective amount of shogaols is combined with one or more of components selected from the group consisting of *Terminalia chebula* family Combretaceae, *Terminalia bellerica* family Combretaceae, *Emblica officinalis* family Euphrobiaceae, *Inula helenium* family Compositae, *Rheum palmatum* family Polygonaceae, *Gentiana lutea* family Gentianaceae, sodium sulfate, sodium chloride and sodium bicarbonate.

\* \* \* \* \*